United States Patent [19]

Verga et al.

[11] Patent Number: 4,698,432
[45] Date of Patent: Oct. 6, 1987

[54] PROCESS FOR THE RESOLUTION OF (±) 2-[2'-(P-FLUOROPHENYL)-5'-BENZOXAZOLYL]-PROPIONIC ACID

[75] Inventors: Alberto Verga, Milan; Oreste Piccolo, Leghorn; Ermanno Valoti, Dalmine, all of Italy

[73] Assignee: Ravizza SpA, Muggio, Italy

[21] Appl. No.: 756,671

[22] Filed: Jul. 19, 1985

[30] Foreign Application Priority Data

Jul. 23, 1984 [IT] Italy ............................... 22009 A/84

[51] Int. Cl.$^4$ ............................................ C07D 263/54
[52] U.S. Cl. ..................................................... 548/224
[58] Field of Search ........................................ 548/224

[56] References Cited

U.S. PATENT DOCUMENTS 4,246,164  1/1981  Felder et al. ........................ 562/401

FOREIGN PATENT DOCUMENTS 655106  3/1986  Switzerland .
1495488  12/1977  United Kingdom .

OTHER PUBLICATIONS

International Pharmaceutical Patents Co., Chem. Abst. 89-24287n (1978), eq. UK 1495488.
Felder et al., Chem. Abst. 93-132285b, eq. U.S. Pat. No. 4,246,164.
Von Morze, Chem. Abst. 101-23151t, eq. European Pat. Off. 95901.

Primary Examiner—Donald G. Daus
Assistant Examiner—Cecilia Shen
Attorney, Agent, or Firm—Stevens, Davis, Miller & Mosher

[57] ABSTRACT

A process for the resolution of (±) 2-[2'-(p-fluorophenyl)-5'-benzoxazolyl]-propionic acid, indicated for brevity as (±)-FBP, by treatment with (−)N-R-glucamine, indicated for brevity as NRG and in which R is an alkyl or cycloalkyl radical, followed by fractional crystallization of the mixture of the diastereoisomer salts obtained, and by separation of the precipitate, from which, by hydrolysis, (±)-FBP is obtained with the required purity characteristics. The levorotatory antipode, (−)-FBP, is racemized, preferably by the formation of one of its esters, which is then hydrolyzed to give the (±)-FBP, which is recycled to the treatment with NRG. (+)-FBP and (−)-FBP salts with NRG obtained by said process.

18 Claims, No Drawings

PROCESS FOR THE RESOLUTION OF (±) 2-[2'-(P-FLUOROPHENYL)-5'-BENZOXAZOLYL]-PROPIONIC ACID

This invention relates to a process for the resolution of (±) 2-[2'-(p-fluorophenyl)-5'-benzoxazolyl]-propionic acid, indicated for brevity as (±)-FBP. More particularly, the invention relates to a process for the resolution of (±)-FBP, based on treatment with (−)N-R-glucamine, indicated for brevity as NRG, in which R is an alkyl radical of 1 to 12 carbon atoms, or a cycloalkyl radical of 3 to 6 carbon atoms, in order to obtain (+) 2-[2'-(p-fluorophenyl)-5'-benzoxazolyl]-propionic acid, indicated for brevity as (+)-FBP, whereas the levorotatory antipode, namely (−) 2-[2'-(p-fluorophenyl)-5'-benzoxazolyl]-propionic acid, indicated for brevity as (−)-FBP, is racemised, preferably by means of the formation of one of its esters, and is recycled to the treatment with NRG. (+)-FBP acid is an effective anti-inflammatory agent, which is considerably more powerful than phenylbutanzone and considerably less toxic. Its anti-inflammatory activity exceeds that of the corresponding raceme acid, and thus obtaining it with adequate optical purity, such that its specific rotation $[\alpha]_D^{20}$ is between +60 and +68 (c=2% DMF), is of considerable interest. The preparation of (+)-FBP is described for example in British Pat. No. 1,495,488 and in Italian Pat. No. 22454 A/82, which state that in spite of numerous attempts at isolating (+)-FBP from the corresponding raceme acid by fractional crystallisation of diastereoisomer salts, this method does not give positive results, and a process is described for obtaining (+)-FBP from (−) 2-(4'-hydroxy-3'-nitrophenyl)-propionitrile by various stages which should be carried out under non-racemising conditions. In reality, the (+)-FBP obtained in this manner requires further purification process in order to obtain the required degree of optical purity. We have now surprisingly found that it is possible to obtain (+)-FBP by resolution of (±)-FBP, operating by a process which enables said product to be obtained with a high yield and a high degree of optical purity.

Further advantages of the process according to the present invention are the use of easily recoverable economical solvents, a low ratio of solvent volume to the quantity of raceme substrate, the use of a low-cost, easily recoverable resolving agent, and a high recovery yield of the undesired antipode, which is racemised and recycled. The process according to the present invention is characterised by being carried out in accordance with the following stages:

(a) salification of the (±)-FBP with NRG in an organic solvent, in the presence or absence of other bases, where (±)-FBP and NRG have the aforesaid meanings;

(b) fractional crystallisation, by means of which essentially the (+)-FBP/NRG salt precipitates;

(c) filtration, in order to separate the crystallised (+)-FBP/NRG salt from the mother liquors;

(d) hydrolysis of the (+)-FBP/NRG in order to obtain the required (+)-FBP;

(e) racemisation of the (−)-FBP contained in the mother liquors of stage (c), to obtain the (±)-FBP, which is recycled to stage (a).

These and further characteristics and advantages of the process according to the present invention will be more apparent from the description given hereinafter which relates to preferred methods of implementing the invention, and is given for illustrative purpose. The (±)-FBP and the NRG are dissolved under hot conditions in an organic solvent, in which the (+)-FBP/NRG and (−)-FBP/NRG salts form. The quantity of NRG used varies from 0.5 to 1 mole per mole of (±)-FBP. When less than 1 mole of NRG is used, the salification of the acid can be completed by adding an organic or inorganic base such as an alkylamine, an alkaline or alkaline-earth hydroxide, ammonium hydroxide etc.

The use of less than 1 mole of NRG is preferable for economical reasons.

The operation is carried out at a (±)-FBP concentration of between 1.00 and 0.01 g/l and preferably between 0.25 and 0.05 g/l, at a temperature of between 0° and 150° C., and preferably between 20° and 100° C.

The solvent used can be alcohols, such as methanol, ethanol and i.propanol, aromatic hydrocarbons such as benzene and toluene, esters such as ethyl acetate, ketones such as acetone and methylethylketone, halogenated hydrocarbons such as chloroform, or mixtures of said solvents.

If necessary, water can also be added to the solvent in a quantity sufficient to solubilise under hot conditions all the organic compounds which have been added to the solvent. The reaction mixture obtained as heretofore described is cooled slowly, under agitation, to a temperature of between 0° C. and 100° C. to obtain fractional crystallisation with the preferential precipitation of the (+)-FBP/NRG.

The (+)-FBP/NRG salt is separated by filtration at a temperature of preferably between 0° C. and 30° C., and is washed with solvent. It is then suspended in water at a temperature of 25°–100° C. and then treated with organic mineral acids such as acetic acid, HCl or $H_2SO_4$ in order to release the (+)-FBP acid, which can be recovered by simple filtration, or by extraction with a solvent followed by the evaporation of this latter. In this manner, the (+)-FBP is obtained with a yield of between 70% and 90% and having specific rotation $[\alpha]_D^{20}$ of between +60 and +68 (c=2% DMF).

The fractional precipitation of the (+)-FBP/NRG salt can be repeated if the specific rotation of the released (+)-FBP does not fall within the indicated limits. The mother liquors originating from the fractional crystallisation, and containing a $C_1$–$C_{12}$ alcohol either initially or after suitable addition, are acidified with mineral acid and heated to a temperature of between 30° C. and the boiling point of the mixture under reflux, for a time of between 1 and 10 hours, to obtain the formation of the corresponding (−)-FBP ester. This mixture is then treated at a temperature of between 25° C. and the reflux temperature with a base such as Na or K hydroxide or methylate in a molar ratio with respect to the (−)-FBP ester of between 1.5 and 5.0. After acidification, this mixture provides an FBP acid with a $[\alpha]_D^{20}$ of between 0 and −6 (c=2% DMF), which is recycled to the first stage.

The (−)-FBP can also be racemised directly in an acid or basic environment by known methods.

The NRG is recovered by known methods, and then recycled to the first stage.

The FBP and NRG salts are new products.

The following examples of the process according to the present invention are given by way of non-limiting illustration.

EXAMPLE 1

A suspension of 4.0 g (0.02 moles) of (−) N-methyl-glucamine in 30 ml of methanol was heated to 60° C., and a solution of 11.4 g (0.04 moles) of (±)-FBP and 2.0 g (0.02 moles) of triethylamine in 20 ml of methanol, also heated to 60° C., was added.

The solution thus obtained was allowed to cool slowly to a temperature of 20° C. so that the (+)-FBP salt crystallised. The precipitate was filtered off and washed on the filter with methanol.

A sample of N-methyl-glucamine dry salt had a melting point of 173°–174° C. and a specific rotation $[\alpha]_{436}^{20}$ of −3.5 (c=1% in DMF). The precipitated was suspended in 50 ml of water, and the mixture was acidified to pH 1 with a 37 weight % aqueous solution of HCl. After extracting with ethyl acetate and evaporating the solvent, 4.9 g of (+)-FBP with a specific rotation $[\alpha]_D^{20}$ of +67.6 (c=2% DMF) were obtained.

6.1g of (−)-FBP with a specific rotation $[\alpha]_D^{20}$ of −47.3 (c=2% in DMF) were obtained from the mother liquors after concentrating the solvent and recovering by an analogous procedure.

EXAMPLE 2

Example 1 was repeated, operating under the described conditions, but with the difference that the (−)-N-methyl-glucamine was added in solid form to 50 ml of a methanolic solution of the other components heated to 60° C.

4.7 g of (+)-FBP with a specific rotation $[\alpha]_D^{20}$ of +67.8 (c=2% in DMF) were obtained.

EXAMPLE 3

Example 1 was repeated, operating under the described conditions but with the difference that a total of 50 ml of ethanol was used instead of methanol. 4.9 g of (+)-FBP with a specific rotation $[\alpha]_D^{20}$ of +64.8 (c=2% in DMF) were obtained.

EXAMPLE 4

Example 1 was repeated, operating under the described conditions but with the difference that the total of 80 ml of i.propanol were used instead of methanol. 5.5 g of (+)-FBP with a specific rotation $[\alpha]_D^{20}$ of +50.4 (c=2% DMF) were obtained.

EXAMPLE 5

Example 1 was repeated, operating under the described conditions but with the difference that a total of 80 ml of ethyl acetate was used instead of methanol. 5.0 g of (+)-FBP with a specific rotation $[\alpha]_D^{20}$ of +45.1 (c=2% DMF) were obtained.

EXAMPLE 6

Example 1 was repeated, operating under the desired conditions but with the difference that a total of 80 ml of a toluene-methanol mixture of volumetric ratio 7:3 were used instead of methanol alone. 5.4 g of (+)-FBP with a specific rotation $[\alpha]_D^{20}$ of +45.9 (c=2% DMF) were obtained.

EXAMPLE 7

Example 6 was repeated, operating under the described conditions but with the difference that 110 ml of the toluene-methanol mixture were used. 4.8 g of (+)-FBP with a specific rotation $[\alpha]_D^{20}$ of +64.3 (c=2% DMF) were obtained.

EXAMPLE 8

Example 1 was repeated as far as the crystallisation of the (+)-FBP salt, which was filtered off and washed on the filter with methanol. The mother liquors originating from said crystallisation and washing operations, and containing the levorotatory antipode, were acidified by adding 1.4 ml of 96% sulphuric acid, and were kept for 3 hours boiling under reflux. 6 g of potassium hydroxide were added, and the mixture was kept boiling under reflux for 3 hours.

After adding 5 ml of water and distilling the methanol, the mixture was acidified with hydrochloric acid, and the organic phase extracted with ethyl acetate. (Alternatively, the mixture was acidified with acetic acid, and the FBP acid was recovered by filtration).

After concentration the solvent, 5.8 g of an FBP acid with a specific rotation $[\alpha]_D^{20}$ of −5.0 (c=2% DMF) were recovered, and could be recycled to the first stage without further purification.

EXAMPLE 9

6.3 g (0.021 moles) of (−)-FBP methyl ester with a specific rotation $[\alpha]_D^{20}$ of −36.2 (c=2% DMF) and obtained from (−)-FBP with a specific rotation $[\alpha]_D^{20}$ of −47.3 (c=2% DMF), were treated with 2.7 g of KOH in 60 ml of methanol under reflux for 2 hours. After adding 5 ml of water and then repeating the recovery procedure of Example 8, 5.7 g of FBP acid with a specific rotation $[\alpha]_D^{20}$ of −2.4 (c=2% DMF) were obtained.

EXAMPLE 10

10.0 g (0.035 moles) of (−)-FBP with a specific rotation $[\alpha]_D^{20}$ of −50.4 (c=2% DMF) were heated in 85% phosphoric acid for 5 hours at 130° C. 8.9 g of (±)-FBP were obtained.

EXAMPLE 11

15.0 g of (+)-FBP acid having a specific rotation of $[\alpha]_D^{20}$ of +74 (DMF) were converted to the corresponding N-methyl-glucamine salt by adding 10.3 g of NMG in 50 ml of methanol.

Said salt after crystallization had a melting point of 174°–176° C. and the following specific rotations (c=1% in DMF): $[\alpha]_D^{20}$ of +0.2; $[\alpha]_{578}^{20}$ of 0.0; $[\alpha]_{546}^{20}$ of −0.1; $[\alpha]_{436}^{20}$ of −2.2.

In the same manner, starting from an (−)-FBP acid having a specific rotation $[\alpha]_D^{20}$ of −74.5 (DMF), a salt of NMG was prepared which, after crystallization from acetone, had a melting point of 135°–137° C. and the following specific rotations (c=1% in DMF); $[\alpha]_D^{20}$ of −27.9; $[\alpha]_{578}^{20}$ of −29.1; $[\alpha]_{546}^{20}$ of −32.7; $[\alpha]_{436}^{20}$ of −53.0.

We claim:

1. A process for the resolution of (±) 2-[2'-(p-fluorophenyl)-5'-benzoxazolyl]propionic acid, indicated for brevity as (±)-FBP, in order to produce (+) 2-[2'-(p-fluorophenyl)-5'-benzoxazolyl]propionic acid, indicated for brevity as (+)-FBP, characterised by comprising the following stages:

(a) salification of the (±)-FBP with (−)N-R-glucamine, indicated for brevity as NRG and in which R is $C_1$–$C_{12}$ alkyl radical or a $C_3$–$C_6$ cycloalkyl radical, in the presence or absence of other bases, and in an organic solvent;

(b) fractional crystallisation, by means of which essentially the (+)-FBP/NRG salt precipitates;

(c) filtration, in order to separate the crystallised (+)-FBP/NRG salt from the mother liquors;
(d) hydrolysis of the (+)-FBP/NRG in order to obtain the required (+)-FBP;
(e) racemisation of the (−)-FBP contained in the mother liquors of stage (c), in order to obtain (±)-FBP, which is recycled to stage (a).

2. A process as claimed in claim 1, characterised in that said salification of the (±)-FBP with NRG is effected by using between 0.5 and 1 mole of NRG per mole of (±)-FBP, the salification of the acid being able to be completed by adding an organic or inorganic base.

3. A process as claimed in the preceding claims, characterised in that the salification of the acid is completed by adding an alkaline or alkaline-earth hydroxide, or ammonium hydroxide.

4. A process as claimed in claims 1 and 2, characterised in that the salification of the acid is completed by adding triethylamine.

5. A process as claimed in claim 1, characterised in that said salification of the (±)-FBP with NRG is effected in organic solvents such as alcohols containing between 1 and 4 carbon atoms, aromatic hydrocarbons, esters, ketones or halogenated hydrocarbons, or in mixtures of said solvents, possibly in the presence of water.

6. A process as claimed in claim 1, characterised in that said salification of the (±)-FBP with NRG is effected in solvents such as methanol and ethanol.

7. A process as claimed in claim 1, characterised in that said salification of the (±)-FBP with NRG is effected by using a (±)-FBP concentration of between 1 and 0.01 g/l, and preferably between 0.25 and 0.05 g/l.

8. A process as claimed in claim 1, characterised in that said salifiction of the (±)-FBP with NRG is effected at a temperature of between 0° and 150° C., and preferably between 20° C. and 100° C.

9. A process as claimed in claim 1, characterised in that said fractional crystallisation is effected by slowly cooling the reaction mixture, under agitation, to a temperature of between 0° C. and 100° C., and preferably between 0° C. and 30° C.

10. A process as claimed in claim 1, characterised in that said filtration for separating the crystallised (+)-FBP/NRG salt is effected preferably at a temperature of between 0° and 30° C.

11. A process as claimed in claim 1, characterised in that said hydrolysis of the (+)-FBP/NRG is effected preferably by treatment with an organic or mineral acid.

12. A process as claimed in claim 1, characterised in that said racemisation is effected after inverting the (−)-FBP into one of its esters, by treating this latter with a strong base.

13. A process as claimed in claim 12, characterised in that said formation of the (−)-FBP ester is effected in situ by treatment with mineral acid.

14. A process as claimed in claim 12, characterised in that said formation of the (−)-FBP ester is effected by heating, preferably to boiling point under reflux.

15. A process as claimed in claim 12, characterised in that, after the racemisation, an FBP acid with a specific rotation $[\alpha]_D^{20}$ of between 0 and −6 (c=2% DMF) is obtained by saponification followed by acidification of the reaction mixture.

16. A process as claimed in claim 1, characterised in that said racemisation of the (−)-FBP is effected by treatment with acid or with a base.

17. N-alkyl-glucamine and N-cycloalkyl-glucamine salts of (+)-2-[2'-(p-fluorophenyl)-5'-benzoxazolyl]-propionic acid.

18. N-alkyl-glucamine and N-cycloalkyl-glucamine salts of (−)-2-[2'-(p-fluorophenyl)-5'-benzoxazolyl]-propionic acid.

* * * * *